United States Patent
Qi et al.

(10) Patent No.: US 10,213,176 B2
(45) Date of Patent: Feb. 26, 2019

(54) APPARATUS AND METHOD FOR HYBRID PRE-LOG AND POST-LOG ITERATIVE IMAGE RECONSTRUCTION FOR COMPUTED TOMOGRAPHY

(71) Applicants: Toshiba Medical Systems Corporation, Otawara-shi (JP); The Regents of the University of California, Oakland, CA (US)

(72) Inventors: Jinyi Qi, Davis, CA (US); Guobao Wang, Woodland, CA (US); Wenli Wang, Briarcliff Manor, NY (US); Jian Zhou, Buffalo Grove, IL (US); Zhou Yu, Wilmette, IL (US)

(73) Assignees: TOSHIBA MEDICAL SYSTEMS CORPORATION, Otawara-shi (JP); The Regents of the University of California, Oakland, CA (US)

(*) Notice: Subject to any disclaimer, the term of this patent is extended or adjusted under 35 U.S.C. 154(b) by 0 days.

(21) Appl. No.: 15/140,187

(22) Filed: Apr. 27, 2016

(65) Prior Publication Data
US 2017/0311918 A1    Nov. 2, 2017

(51) Int. Cl.
*G06K 9/00* (2006.01)
*A61B 6/00* (2006.01)
(Continued)

(52) U.S. Cl.
CPC ............ *A61B 6/5235* (2013.01); *A61B 6/032* (2013.01); *A61B 6/5205* (2013.01);
(Continued)

(58) Field of Classification Search
CPC ..... A61B 3/102; A61B 5/0033; A61B 5/0073; A61B 6/025; A61B 6/03; A61B 6/032;
(Continued)

(56) References Cited

U.S. PATENT DOCUMENTS 6,507,633 B1 * 1/2003 Elbakri ................. G06T 11/006
                                                                 378/4
8,538,114 B2    9/2013 Yang et al.
(Continued)

OTHER PUBLICATIONS

Lin Fu et al., "Comparison Between Pre-log and Post-log Statistical Models in Low-Dose CT Iterative Reconstruction", 2014 IEEE, 10 pages.

*Primary Examiner* — Jose L Couso
(74) *Attorney, Agent, or Firm* — Oblon, McClelland, Maier & Neustadt, L.L.P.

(57) ABSTRACT

A method and apparatus is provided to iteratively reconstruct a computed tomography (CT) image using a hybrid pre-log and post-log iterative reconstruction method. A pre-log formulation is applied to values of the projection data that are less than a threshold (e.g., X-ray intensities corresponding to high absorption trajectories). The pre-log formulation has better noise modeling and better image quality for reconstructed images, but is slow to converge. Projection data values above the threshold are processed using a post-log formulation, which has fast convergence but poorer noise handling. However, the poorer noise handling has little effect on high value projection data. Thus, the hybrid pre-log and post-log method provides improved image quality by more accurately modeling the noise of low count projection data, without sacrificing the fast convergence of the post-log method, which is applied to high-count projection data.

20 Claims, 8 Drawing Sheets

(51) Int. Cl.
*A61B 6/03* (2006.01)
*G06T 11/00* (2006.01)

(52) U.S. Cl.
CPC .......... *A61B 6/5258* (2013.01); *G06T 11/006* (2013.01); *G06T 2211/424* (2013.01)

(58) Field of Classification Search
CPC ..... A61B 6/037; A61B 6/4085; A61B 6/4241; A61B 6/461; A61B 6/5205; A61B 6/5217; A61B 6/5258; A61B 8/13; A61B 2090/376–2090/3762; A61B 2090/3735; G06T 5/002; G06T 5/20; G06T 5/50; G06T 7/0012; G06T 11/003; G06T 11/005; G06T 11/006; G06T 11/008; G06T 2207/10072; G06T 2207/10081; G06T 2207/10108; G06T 2207/10116; G06T 2207/20008; G06T 2207/30004; G06T 2211/408; G06T 2211/421; G06T 2211/424; G06T 2211/428; G06T 2211/432; G01T 1/4642; G01T 1/17; G01T 1/2985; G06K 9/36; G06K 7/1099; G01N 23/046; G01N 2223/419; G01N 2233/1016; H04N 5/32; H04N 5/325; H04N 2201/0412; Y10S 378/901; Y10S 430/167; Y10S 430/168

See application file for complete search history.

(56) References Cited

U.S. PATENT DOCUMENTS

| | | |
|---|---|---|
| 8,712,134 B2 | 4/2014 | Zamyatin et al. |
| 8,885,903 B2 | 11/2014 | Thibault et al. |
| 8,948,337 B2 | 2/2015 | Pack |
| 9,036,885 B2 * | 5/2015 | Elad ............... G06T 11/006 378/21 |
| 9,706,972 B1 * | 7/2017 | Ahn ............... A61B 6/5235 |

* cited by examiner

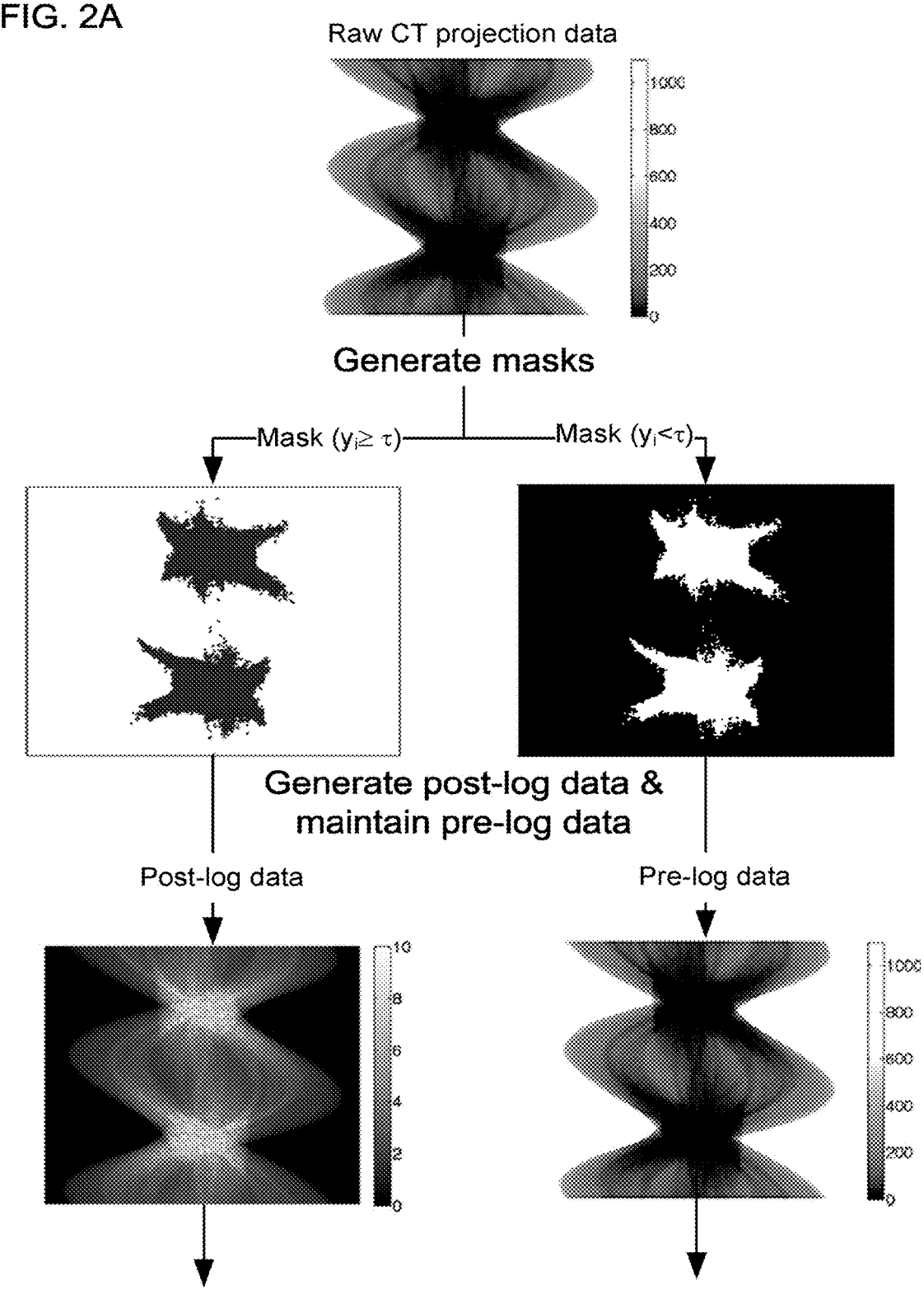

Partial pre-log data

Partial post-log data

APPARATUS AND METHOD FOR HYBRID PRE-LOG AND POST-LOG ITERATIVE IMAGE RECONSTRUCTION FOR COMPUTED TOMOGRAPHY

FIELD

This disclosure relates to iterative image reconstruction using computed-tomography (CT) projection data, and, more particularly, to using a cost function combining pre-log and post log processing methods to reconstruct an image by finding an argument that solves the optimization problem of the cost function.

BACKGROUND

X-ray computed tomography (CT) has found extensive clinical applications in cancer, heart, and brain imaging. As CT has been increasingly used for cancer screening and pediatric imaging, there has arisen a push to reduce the radiation dose of clinical CT scans to become as low as reasonably achievable. Thus, iterative image reconstruction has been playing a more significant role in CT imaging. Iterative image reconstruction algorithms, as compared with traditional analytical algorithms, are promising in reducing the radiation dose while improving the CT image quality.

In X-ray computed tomography (CT), iterative reconstruction can be used to generate images. While there are various iterative reconstruction (IR) methods, such as the algebraic reconstruction technique, one common IR method is optimizing the expression $$\operatorname*{argmin}_{x}\{\|x-\ell\|_W^2 + \beta U(x)\}$$

to obtain the argument x that minimize the expression. For example, in X-ray CT A is the system matrix that represents X-ray trajectories (i.e., line integrals) along various rays from a source through an object OBJ to an X-ray detector (e.g., the X-ray transform corresponding to projections through the three-dimensional object OBJ onto a two-dimensional projection image l), l represents projection images taken at a series of projection angles and corresponding to the log-transform of the measured X-ray intensity at the X-ray detector, and x represents the reconstructed image of the X-ray attenuation of the object OBJ. The notation $\|g\|_W^2$ signifies a weighted inner product of the form $0.5 \times g^T W g$, wherein W is the weight matrix. For example, the weight matrix W can weigh the pixel values according to their noise statistics (e.g., the signal-to-noise ratio), in which case the weight matrix W is diagonal when the noise of each pixel is statistically independent. The data-matching term $\|Ax-l\|_W^2$ is minimized when the forward projection A of the reconstructed image x provides a good approximation to all measured projection images l. In the above expression, $U(x)$ is a regularization term, and $\beta$ is a regularization parameter that weights the relative contributions of the data-matching term and the regularization term.

IR methods augmented with regularization can have several advantages over other reconstruction methods such as filtered back-projection. For example, IR methods augmented with regularization can produce high-quality reconstructions for few-view projection data and in the presence of significant noise. For few-view, limited-angle, and noisy projection scenarios, the application of regularization operators between reconstruction iterations seeks to tune the final and/or intermediate results to some a priori model. For example, enforcing positivity for the attenuation coefficients can provide a level of regularization based on the practical assumption that there are no regions in the object OBJ that cause an increase (i.e., gain) in the intensity of the X-ray radiation.

Other regularization terms can similarly rely on a priori knowledge of characteristics or constraints imposed on the reconstructed image. For example, minimizing the "total variation" (TV) in conjunction with projection on convex sets (POCS) is also a very popular regularization scheme. The TV-minimization algorithm assumes that the image is predominantly uniform over large regions with sharp transitions at the boundaries of the uniform regions, which is generally true for an image of a discrete number of organs, each with an approximately constant X-ray absorption coefficient (e.g., bone having a first absorption coefficient, the lungs having second coefficient, and the heart having a third coefficient). When the a priori model corresponds well to the image object OBJ, these regularized IR algorithms can produce impressive images even though the reconstruction problem is significantly underdetermined (e.g., few-view scenarios), missing projection angles, or noisy.

While the above formulation of the IR method, which uses post-log projection data (i.e., projection data that has been converted from intensity to attenuation by calculating the logarithm of the intensity measurements), can generate better quality images at low dose than filtered-back-projection methods, a continued push to reduce radiation dosage to patients creates pressures and incentives to provide even better image reconstruction at lower X-ray dosages. Tomographic image reconstruction for low-dose CT is increasingly challenging as dose continues to be reduced in clinical applications, and, due to electronic noise, data may contain negative values for which logarithm is undefined. Pre-log methods and post-log methods have been separately proposed to improve various aspects of CT image reconstruction, and each type of method has its own advantages and disadvantages. For example, pre-log methods have the disadvantage of slow convergence due to the nonlinear transformation from image to measurement, but pre-log methods also have the advantage that, in theory, they can improve image quality for low-dose data by accurately modeling the noise. On the other hand, the post-log methods have the advantage of fast convergence, but a disadvantage that, for low-count CT data, image quality can be relatively poor due to noise amplification in the logarithm calculation used to convert the projection data from intensity to attenuation.

BRIEF DESCRIPTION OF THE DRAWINGS

A more complete understanding of this disclosure is provided by reference to the following detailed description when considered in connection with the accompanying drawings, wherein:

FIG. 2A shows a first half of a graphical representation of a method for hybrid pre-log and post-log IR that generates post-log data and then masks the post-log data and pre-log data, according to one implementation;

DETAILED DESCRIPTION

Figure 1:
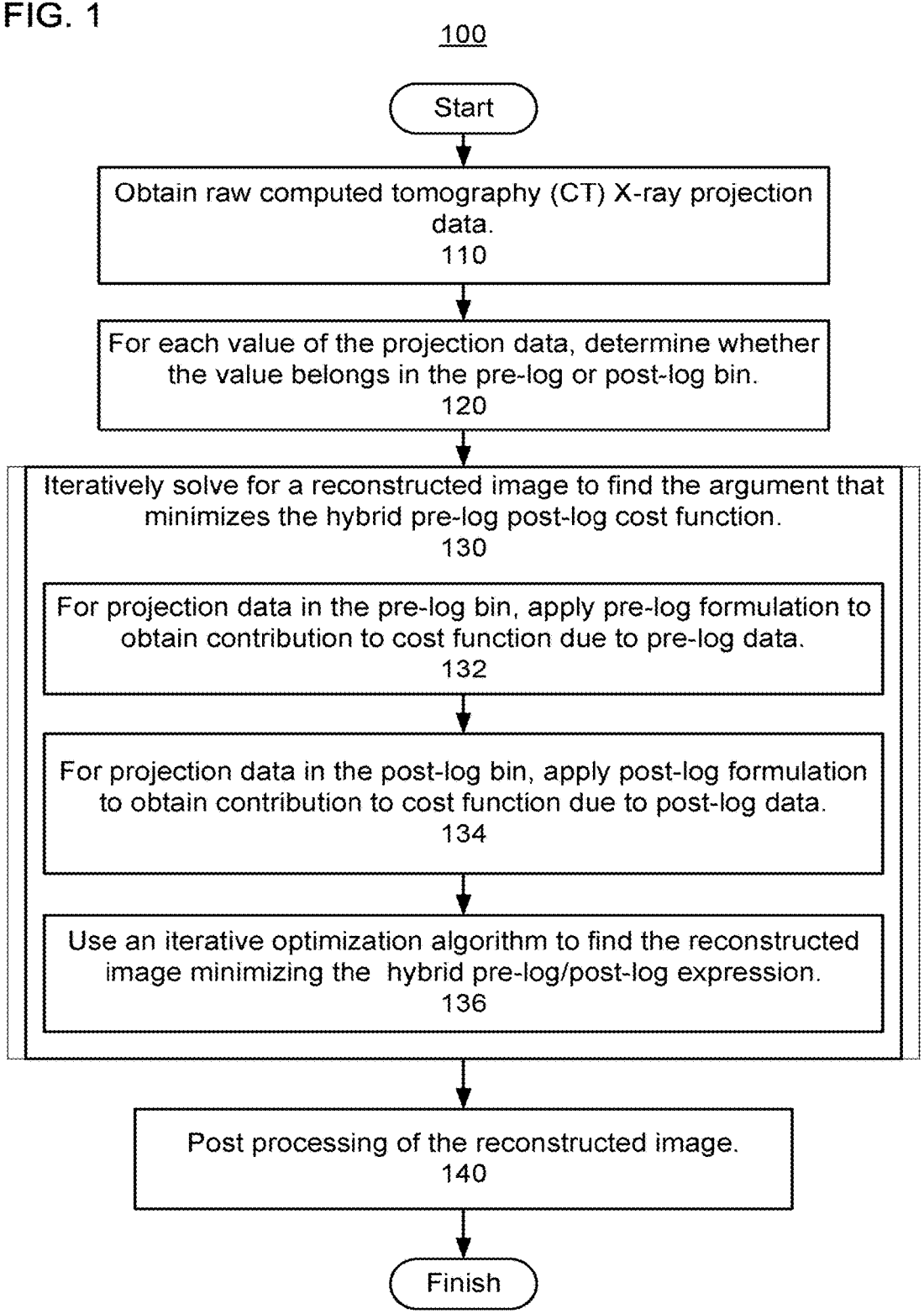
FIG. 1 shows a flow diagram of a method, according to one implementation, for hybrid pre-log and post-log iterative reconstruction (IR) using computed tomography projection data.

Both post-log iterative reconstruction (IR) methods and pre-log IR methods have their separate benefits and challenges. Many of these challenges can be overcome using a hybrid method that integrates the pre-log model and post-log model together to secure the benefits of both methods. This hybrid method is advantageous for overcoming the increasing demand to reduce radiation dosages in clinical computed tomography (CT) applications. On the one hand, IR methods performed in the pre-log domain can, in practice, suffer from slow convergence due to the nonlinear transformation from image to measurement, but, for low-dose CT data, IR methods performed in the pre-log domain can have the benefit of improved image quality attributable to their accurate noise models. On the other hand, IR methods performed in the post-log domain can have fast convergence, but the resulting image quality may be suboptimal for low-count CT data due to the log calculation. The log calculation can be sensitive to noise and can amplify measurement noise when the dose is low and is undefined for negative measurements.

The hybrid method described herein integrates the pre-log model and post-log model together to conquer the disadvantages of the pre-log and post-log methods taken separately. The hybrid method can use a threshold parameter to sort the CT projection data (i.e., raw pre-log data) into post-log data having values greater than the threshold and pre-log data having values less than the threshold. The post-log data and pre-log data are then operated on using respective post-log and pre-log data processing methods. By way of example and not by limitation, the post-log data can be operated on using a weighted-least-squares model and the pre-log data can be operated on using a shifted-Poisson model. Advantageously, the hybrid method described herein can achieve faster convergence than using only a pre-log method (e.g., the pre-log shifted Poisson likelihood method) and can achieve better image quality than using only a post-log method (e.g., a weighted least squares method).

Pre-log methods and post-log methods represent types of tomographic image reconstruction methods for CT. In the pre-log method, the CT image can be directly reconstructed from the raw measurement using either the complex compound Poisson likelihood or approximate statistical models such as the shifted-Poisson model, for example. In the post-log method, the logarithm of a ratio is calculated, the ratio being between a blank scan (e.g., using an empty CT scanner) and a raw scan (e.g., with an object OBJ that is to be imaged). The result is post-log sinogram data representing line integrals (i.e., projections) of the X-ray attenuation through the object OBJ. IR methods, such as the IR filtered back-projection (FBP) reconstruction or penalized weighted least squares (PWLS) method, can then be used to reconstruct the CT image from the sinogram data.

First the pre-log method is considered. In the pre-log method, raw CT measurements are operated on directly. For example, the pre-log method can utilize an accurate or well approximated statistical model of measurement noise (e.g. the shifted-Poisson model). Thus, the pre-log method has the potential to improve image quality in low-dose CT. However, the data model for X-ray transmission is nonlinear, resulting in a complex optimization problem to solve. Although existing optimization approaches like the ordered subsets separable paraboloidal surrogate (OS-SPS) algorithm can be efficiently implemented, these algorithms can be slow to converge to the penalized likelihood solution because of the strong coupling between the pre-log domain and the image domain. Thus, if the iterations are constrained within a practical time limit, the pre-log method might not have yet converged to the optimal image quality, and the resultant image might be poor relative to theoretical limits achievable given unlimited time.

Next the post-log method is considered. In certain implementations, a post-log method can be performed using post-log data and a linear transformation between the image and measurement domains (e.g., a system matrix A). The use of a linear model (e.g., a system matrix A) leads to more efficient computation and faster convergence for image reconstruction. While this implementation of the post-log method can work well in conventional CT imaging, this implementation becomes suboptimal when used with low-dose CT in which the count level at each X-ray detector element may be very low, resulting in a high noise contribution to the signal (i.e., counts). The log calculation for sinogram generation in this implementation of the post-log method is sensitive to noise when the count is low, and results in noise amplification that can lead to artifacts and reduced image quality in the reconstructed image.

To reduce noise-induced artifacts, post-log domain sinograms can be first smoothed and/or denoised using statistical iterative methods prior to tomographic image reconstruction. However, there can be a trade-off between smoothing/denoising and introducing biases into the sinogram data resulting in reduced image quality and artifacts. The benefit of iterative image reconstruction can be maximized if both noise and spatial correlations in the smoothed sinograms can be modeled properly. However, accurate and efficient statistical modeling of noise and correlations in the post-log domain is challenging because noise propagation is complicated and the CT scanner can be spatially variant.

To solve the foregoing problems the hybrid methods described herein advantageously combine pre-log and post-log domain data together to accelerate CT image reconstruction and to improve image quality. Thus, the hybrid methods described herein overcome the disadvantages of the individual post-log and pre-log methods. Further, these advantageous results are achieved through the use of a threshold parameter $\tau$ that classifies the pixel values measured by different X-ray detector elements into "high-count" and "low-count" data. Note, the word "pixel" can be used both to designate a value in an array of X-ray intensity/attenuation values corresponding to the projection (e.g., a two-dimensional pixel in a two-dimensional image), and to a value in the reconstructed attenuation image of the object OBJ (e.g., a three-dimensional volume pixel or voxel in a three-dimensional image). In each instance, the intended meaning of word "pixel" will be clear by the context.

For pixel values greater than the threshold τ, the pixel value is determined to be a "high-count" value and will be processed using a post-log method (e.g., a penalized weighted least square method) to achieve fast convergence. For pixel values less than the threshold τ, the pixel value is determined to be a "low-count" value and will be processed using a pre-log method (e.g., a shifted-Poisson model) to improve the image quality by gaining the benefit of the improved statistical noise modeling. Through proper selection of the threshold parameter τ, the hybrid method can achieve a fast convergence similar to the post-log method, but with improved image quality similar to that of the pre-log method.

The statistical processes in CT imaging are generally complicated and can be modeled using compound Poisson distributions. After preprocessing the X-ray detector counts to account for calibrations and data corrections (e.g., beam-hardening, detector nonlinearities, k escape, pileup, etc.), CT data can, in practice, be modeled by independent random variables following a Poisson distribution with additive Gaussian distribution to account for electronic noise in the measurement. The statistical model of the random variable $Y_i$ measured by the detector element i can be described as $$Y_i \sim \text{Poisson}(\bar{y}_i(x)) + \text{Gaussian}(0, \sigma_o^2) \qquad \text{Eq. (1)}$$

wherein $\sigma_o^2$ denotes the standard deviation of electronic noise. The value $\bar{y}_i(x)$ is the expected projection data related to the image of linear material attenuation coefficient x by means of a nonlinear transformation, which is given by $$\bar{y}_i(x) = b_i \exp(-[Ax]_i) + r_i \qquad \text{Eq. (2)}$$

wherein $b_i$ is the measurement in the detector element i by the blank scan, and $r_i$ is the mean of background measurement (e.g., scattered photons). The (i;j)th element of the system matrix A represents the line integral of attenuation for X-ray photons passing through the image pixel j and being detected by the detector element/pixel i.

Inclusion of the electronic noise modeling can improve low-dose CT image reconstruction. However, there is no simple analytical form for the likelihood function of the combined Poisson and Gaussian model in Eq. (1) and therefore use of this model is computationally challenging. Another statistical model is the shifted-Poisson model $$\hat{Y}_i = [Y_i + \sigma_o^2]_+ \sim \text{Poisson}(\bar{y}_i(x) + \sigma_o^2), \qquad \text{Eq. (3)}$$

wherein $[\cdot]_+$ is threshold function that sets negative values to zero. The first two orders of statistical moments (mean and variance) of the shifted-Poisson model can be matched with that of the Poisson-Gaussian model. The shifted-Poisson model is more attractive in practice than other more complex models because it makes computation more tractable.

The realizations of random variable Y in all detector elements can be denoted by $y \in i^{n_i \times 1}$, wherein $n_i$ is the number of detector elements. The pre-log methods can reconstruct the attenuation image x either from the measurement y using a complex likelihood function or from the shifted data $$\hat{Y}_i = [Y_i + \sigma_o^2]_+ \sim \text{Poisson}(\bar{y}_i(x) + \sigma_o^2), \qquad \text{Eq. (4)}$$

using the tractable shifted-Poisson model. In addition to the shifted-Poisson model and the Poisson-Gaussian model, the statistical model can be a Poisson model, a compound Poisson model, or any other statistical distribution or combination of statistical distribution representing the noise in the system. For the shifted-Poisson model, the image estimate is obtained by maximizing the log likelihood function of the shifted-Poisson model, which is given by $$\hat{x} = \arg\max_{x \geq 0} \sum_i [\hat{y}_i \log(\bar{y}_i(x) + \sigma_o^2) - (\bar{y}_i(x) + \sigma_o^2)] - \beta U(x), \qquad \text{Eq. (5)}$$

wherein U(x) is an image roughness penalty and β controls the strength of the regularization. The regularization term U(x) can be determined as the intensity difference between neighboring pixels, which is given by $$U(x) = \sum_j \sum_{k \in \aleph_j} w_{jk} \psi_\delta(x_j - x_k), \qquad \text{Eq. (6)}$$

wherein $\psi_\delta(t)$ is the penalty function, δ is a parameter that controls the smoothness of the penalty function, $w_{jk}$ is the weighting factor related to the distance between pixel j and pixel k in the neighborhood $\aleph_j$. An example of $\psi_\delta(t)$ is the Huber function, which can be expressed as $$\psi_\delta(t) = \begin{cases} \frac{1}{2}t^2, & \delta \geq |t| \\ \delta|t| - \frac{\delta^2}{2}, & \text{otherwise} \end{cases} \qquad \text{Eq. (7)}$$

In addition to the Huber function, the regularization term U(x) can be a quadratic regularization term, a total variation minimization term, or any other regularization term.

In certain implementations, the above optimization problem express in Eq. (5) can be solved by the separable paraboloidal surrogate (SPS) approach with acceleration by ordered subsets (OS), for example. In general any optimization method can be used to solve Eq. (5), including, for example, a gradient-descent method or other known methods. Further examples of optimization methods that can be used to solve the above optimization problem expressed in Eq. (5) include: an augmented-Lagrangian method, an alternating direction-method-of-multiplier method, a Nesterov method, a preconditioned-gradient-descent method, an ordered subset method, or a combination of the foregoing.

The advantages of the pre-log methods include that accurate or well approximated noise modeling is allowed in the raw projection domain, which can benefit low-count image reconstruction for low-dose CT. However, due to the non-linearity of the expected data $\bar{y}_i(x)$ with regard to the image x, the associated computation often requires greater computational resources, and the convergence of the pre-log methods can be slower than that of the post-log methods described herein.

The post-log methods employ a log calculation to remove the nonlinearity in Eq. (2) and simplify the reconstruction problem. In certain implementations, the line integral of the attenuation for each detector element i can be calculated from the measurement $y_i$ by $$\hat{l}_i = \log \frac{b_i}{y_i - r_i}. \qquad \text{Eq. (8)}$$

The expected data of the post-log sinogram $\hat{l}$ can be linearly related to the image to be reconstructed, such that the relation between the post-log sinogram and the reconstructed image x is given by the system-matrix equation $$\bar{l}(x) = Ax. \qquad \text{Eq. (9)}$$

In certain implementations, the image x can be reconstructed from $\hat{l}$ using the penalized weighted least squares (PWLS) formulation, which is given by the expression $$\hat{x} = \underset{x \geq 0}{\operatorname{argmin}} \sum_i \frac{w_i}{2}(\hat{l}_i - \bar{l}_i(x))^2 + \beta U(x), \qquad \text{Eq. (10)}$$

wherein the weighting factor $\{w_i\}$ can represent an approximate inverse variance of $\hat{l}$ that is derived from the Poisson model, $$w_i = \frac{y_i^2}{y_i + \sigma_b^2} \qquad \text{Eq. (11)}$$

The post-log reconstruction problem in Eq. (10) can be solved using any known optimization method such as the OS-SPS algorithm and any of the optimization methods discussed above, for example. The convergence of the optimization method operating on Eq. (10) is usually fast. Even so, the image quality might be suboptimal because $\hat{l}_i$ is a key input in Eq. (10) and $\hat{l}_i$ largely determines the quality of the reconstructed image. However, the calculation of $\hat{l}_i$ using the logarithm in Eq. (8) can become unstable for low signal-to-noise ratios such as those encountered in low-dose CT, because noise in the projection data y can be amplified when the logarithm is taken to generate $\hat{l}$. Accurately modeling the noise of $\hat{l}$ can be difficult because the noise propagation is complicated and the imaging system of the CT scanner can be spatially variant (e.g., the X-ray beam from the CT scanner can be non-uniform). Consequently, noise-induced artifacts can be generated in the reconstructed images when a post-log method is used.

Both pre-log methods and post-log methods have their own advantages and disadvantages, as discussed above. The pre-log methods allow well-approximated noise modeling in the raw projection domain corresponding to improved image quality in theory, but, due to slow convergence of the reconstruction, the image quality achieved in practice with practical time constraints can greatly limit improvements to the image quality. The post-log methods converge rapidly but the image quality can be suboptimal for low-count CT data. The hybrid method described herein overcomes the disadvantages of either pre-log methods or post-log methods taken separately.

The hybrid method reconstructs an image of the object OBJ using the optimization formulation $$\hat{x} = \underset{x \geq 0}{\operatorname{argmin}} \sum_i h_{i,\tau}(\bar{l}_i(x)) + \beta U(x), \qquad \text{Eq. (12)}$$

wherein $\bar{l}_i(x)$ is the expected data of the line integral for detector element i, which is defined by Eq. (9). The function $h_{i,\tau}(l)$ denotes the data fidelity for detector element i with τ as the threshold parameter for choosing between a post-log method and a pre-log method (e.g., the pre-log method can use a shift Poisson model and the post-log method can use a weighted-least-squares model). The same regularization as defined by U(x) in the pre-log and post-log methods can be used for the hybrid method.

The form of $h_{i,\tau}(l)$ in the hybrid method is given by $$h_{i,\tau}(\ell_i) = \begin{cases} \tilde{y}_1(\ell_i) - ([y_i + \sigma_e^2]_+) \log \tilde{y}_1(\ell_i), & y_i < \tau, \\ \frac{1}{2} w_i (\hat{\ell}_i - \ell_i)^2, & y_i \geq \tau, \end{cases} \qquad \text{Eq. (13)}$$

wherein $\tilde{y}_i$ ($l_i$) is the sum of the expected data $\bar{y}_i$ ($l_i$) in Eq. (2) and electronic noise variance, which is given by $$\tilde{y}_i(\ell_i) = b_i \exp(-\ell_i) + r_i + \sigma_e^2 \qquad \text{Eq. (14)}$$

The post-log sinogram $\hat{l}_i$ is defined by Eq. (8) and the weights $w_i$ are given in Eq. (11).

The threshold parameter τ has a significant function in the hybrid method. When τ=−∞, the hybrid method is the same as the post-log method (e.g., PWLS) with fast convergence. As τ increases, the hybrid method approaches the pre-log shifted Poisson solution with statistically efficient image quality. In Eq (13), the parameter τ can be different for different detector elements.

For a specific detector element/pixel i, if the measurement $y_i$ is less than the threshold τ, the shifted-Poisson model will be chosen to take advantage of statistical noise modeling in the pre-log domain to improve image quality based on low-count data. If the measurement $y_i$ is greater than τ, the log calculation for post-log sinogram generation is expected to be robust to the noise amplification of the logarithm function due to the relatively large signal-to-noise ratio. Thus, a post-log method can be used for fast convergence.

By properly choosing the threshold value τ, the hybrid post-log/pre-log image reconstruction method can not only converge quickly, but also generate good image quality compared to existing methods that use either only pre-log data (τ=∞) or post-log data (τ=−∞. In certain implementations, the threshold τ can be chosen to be a predefined function of the standard deviation of the electronic noise $\sigma_{\hat{o}}$, for example. In certain implementations, the threshold τ can be chosen to ensure that the post-log data exceeds a predefined signal-to-noise ratio, and all pixel values having a signal-to-noise ratio below the threshold τ are processed using the pre-log formulation. In certain implementations, the threshold τ can be empirically selected to achieve a predefined image quality. For example, if the image quality of the reconstructed image is less than a predefined figure of merit, then the threshold τ can be increased (up to a certain predefined limit) to achieve a better image quality. In certain implementations, the threshold τ can be set low for early iterations of the optimization method operating on Eq. (12) in order to ensure early rapid convergence, and then the threshold τ can be increased during latter iterations to achieve better final image quality.

Referring now to the drawings, wherein like reference numerals designate identical or corresponding parts throughout the several views, FIG. 1 shows a flow diagram of one implementation of the hybrid method 100. In step 110 of method 100, the projection data $y_i$ are obtained. The projection data $y_i$ can be obtained using measurements performed by a CT scanner, or by retrieving previously generated projection data from a computer-readable memory in which projection data was stored.

In step 120 of method 100, the threshold τ is applied to the projection data $y_i$. Those pixel values $y_i$ of the projection data that are determined to be greater than or equal to the threshold τ are regarded as post-log data and are used to generate the value $\hat{I}_i$ (e.g., using Eq. (8)). Those pixel values $y_i$ of the projection data that are determined to be less than the threshold τ are regarded as pre-log data and are maintained in their pre-log representation $y_i$.

In process 130 of method 100, the cost function given by the summation on the right-hand side of Eq. (12) is calculated using a hybrid formulation, such as Eq. (13). The reconstructed image x (and by extension $\hat{I}_i(x)$) is adjusted to optimize the cost function. Any known optimization method can be used, including those discussed above. In certain implementations, process 130 can be performed using steps 132, 134, and 136.

In step 132 of process 130, the contributions of the pre-log data to $h_{i,\tau}(\hat{I}_i(x))$ are calculated using, for example, a shifted-Poisson model.

In step 134 of process 130, the contributions of the post-log data to $h_{i,\tau}(\hat{I}_i(x))$ are calculated using, for example, a weighted-least-squares (WLS) formulation.

In step 136 of process 130, the cost function is optimized using an optimization method by, for example, comparing the value of the cost function to a predefined stopping criteria and calculating an updated reconstructed image x and value $\hat{I}_i(x)$ when the stopping criteria is not satisfied.

In step 140 of method 100, the reconstructed image can be further processed using post-processing steps and methods. Post-reconstruction processing can include denoising, filtering, and smoothing of the reconstructed image, volume rendering processing, material decomposition, and image difference processing as needed. In certain implementations, step 140 can be omitted.

Figure 2B:
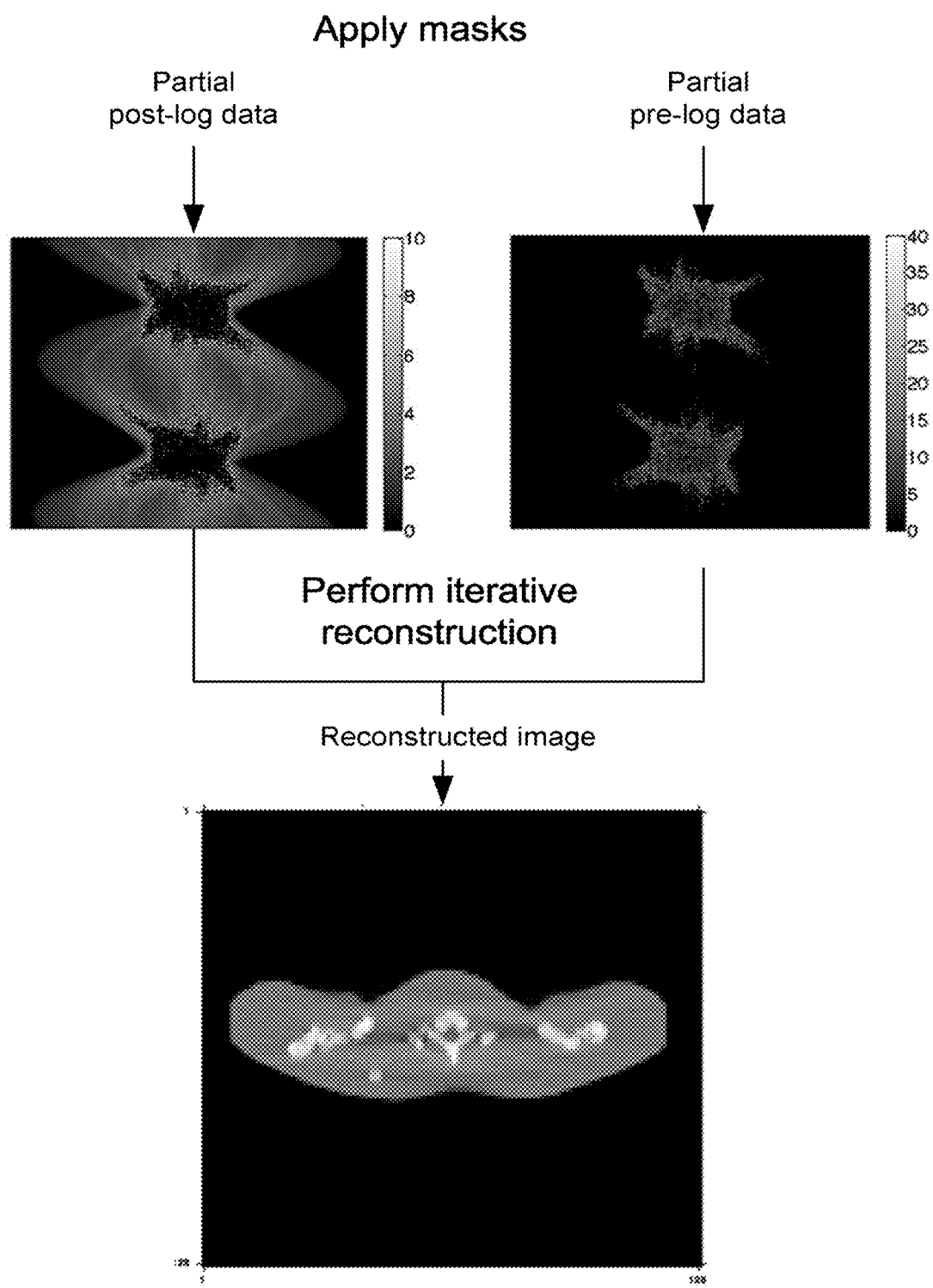
FIG. 2B shows a second half of the graphical representation of the method for hybrid pre-log and post-log IR that generates post-log data and then masks the post-log data and pre-log data.
Figure 3A:
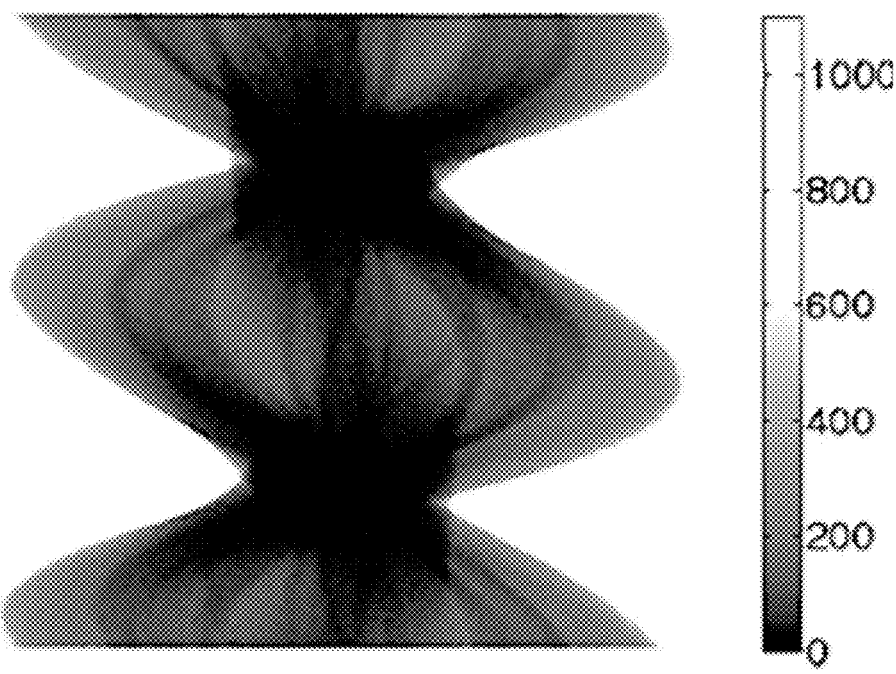
FIG. 3A shows a sinogram plot of an example of pre-log data.
Figure 3B:
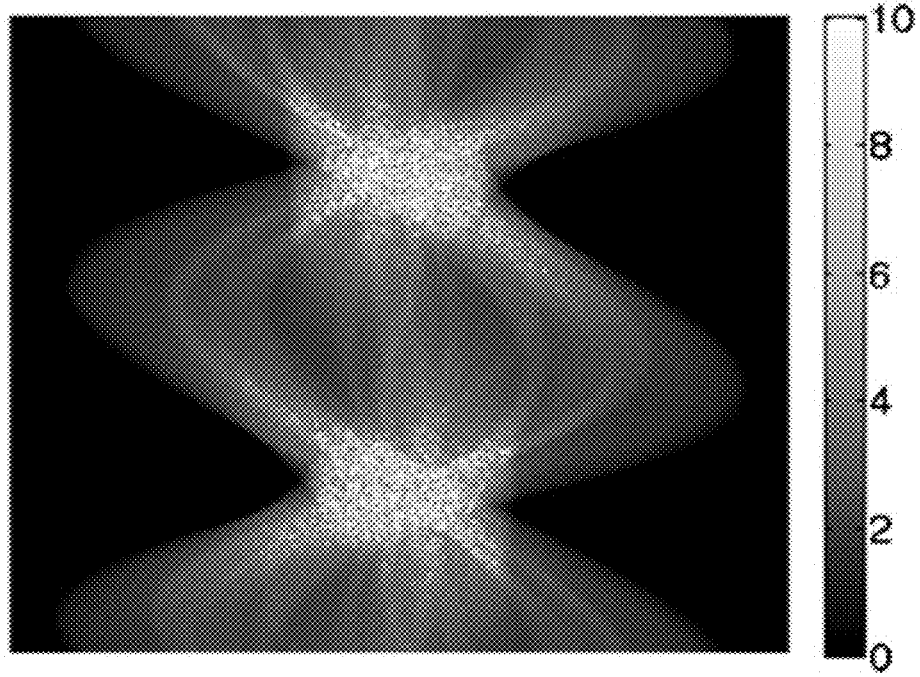
FIG. 3B shows a sinogram plot of an example of post-log data.
Figure 3C:
FIG. 3C shows an example of a mask for the pre-log data.
Figure 3D:
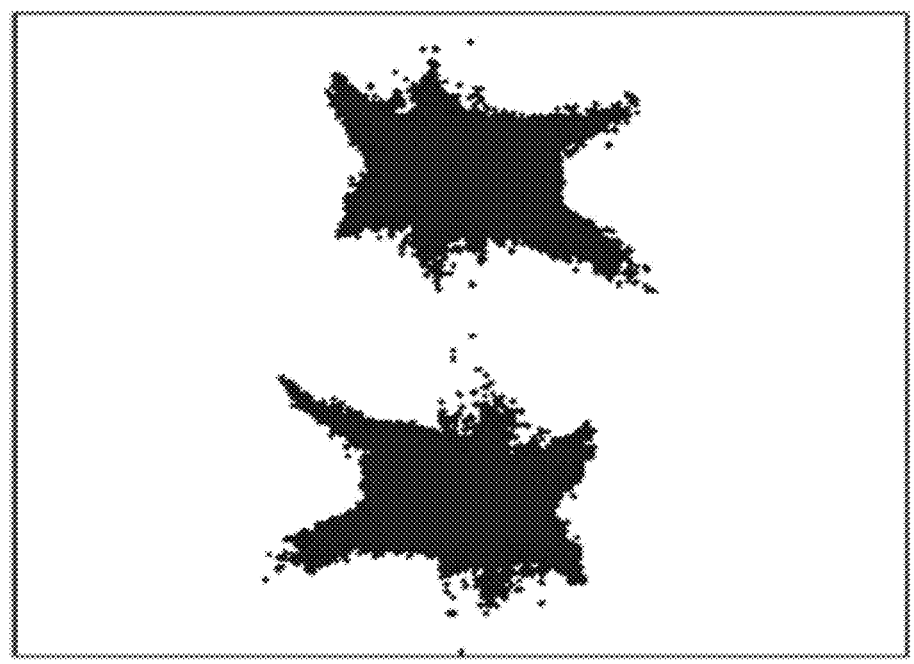
FIG. 3D shows an example of a mask for the post-log data.
Figure 3E:
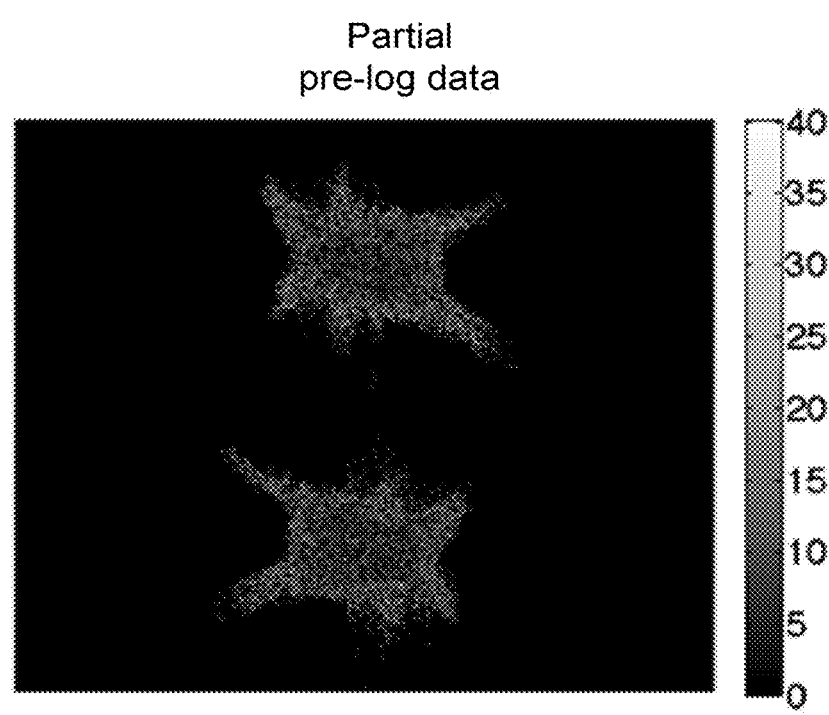
FIG. 3E shows a plot of the masked pre-log data (i.e., partial pre-log data)
Figure 3F:
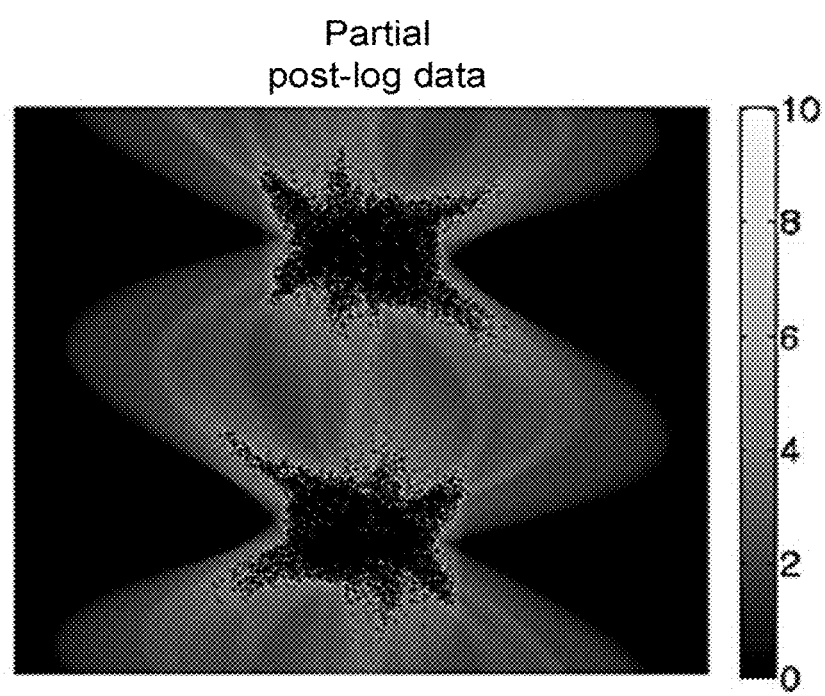
FIG. 3F shows a plot of masked post-log data (i.e., partial post-log data)

FIGS. 2A and 2B shows a graphical representation of one implementation of method 100. At the top of FIG. 2A, the raw CT projection data is shown, which is the same as the pre-log sinogram data. The pre-log sinogram data (raw CT projection data) is also shown in FIG. 3A. Based on a comparison between the pre-log sinogram data and the threshold parameter τ, pre-log and post-log masks can be generated. The pre-log mask is shown in FIG. 3C, and the post-log mask is shown in FIG. 3D. The white pixels of the masks represent pixels of the sinogram data for which the corresponding inequality is satisfied, and the black pixels of the masks represent pixels of the sinogram data for which the corresponding inequality is not satisfied. After generating the masks (or alternatively in parallel with generating the masks), the post-log data is generated (e.g., using Eq. (8)). In certain implementations to improve efficiency, the calculation of the post-log data can be limited to those pixels satisfying the post-log threshold inequality. The post-log sinogram data is shown in FIG. 3B. Next, as shown in FIG. 2B, the masks can be respectively applied to the pre-log and post-log sinogram data, after which the image x is reconstructed by minimizing the cost function in Eq. (12). The partial pre-log data (i.e., the pre-log data after application of the pre-log mask) and the partial post-log data (i.e., the post-log data after application of the post-log mask) are shown in FIGS. 3E and 3F respectively.

In certain implementations, the masks can be generated with reference to other sinogram data rather than the raw CT projection data prior to the logarithm. For example, a preliminary image can be reconstructed from the raw CT projection data, and the masks can be derived using reprojections of the preliminary image. In certain implementations, the raw CT projection data can be downsampled, and then filtered back-projection can be performed using the downsampled data to generate a downsampled preliminarily image. Next, the downsampled preliminarily image can be upsampled to generate a preliminarily image. The preliminarily image can be denoised and/or spatially filtered and then forward projected to generate reprojected CT projection data. The mask can then be generated by comparing the reprojected CT projection data to a threshold. Additionally, the steps of downsampling and upsampling can be omitted, for example, when computational resources are not scarce. Alternatively, denoising and filtering can be applied directly to the raw CT projection data and the denoised/filtered raw CT projection data can be used to generate the masks. Generally, the raw CT projection data can be processed by any method understood by one of ordinary skill in the art to improve the fidelity and predictive qualities of the masks in order to separate the sinogram into regions of low X-ray fluence and regions of medium-to-high X-ray fluence.

In one implementation of the steps shown in FIGS. 2A and 2B, the threshold parameter τ is determined using the standard deviation of electronic noise and count level of CT measurement. For example, $\tau = 4\sigma_e + r_i$ can work well when the blank scan count level of detector element is $b_i = 10^3$. Two masks are then obtained to indicate the X-ray detector elements with measurements less than τ (pre-log mask) and those with measurements equal to or greater than τ (post-log mask). With these masks, the post-log data and pre-log data are assigned values from the projection data. Next, for any detector element/pixel that is assigned to be pre-log data, the shifted-Poisson model is employed for data fidelity; for any detector element assigned to be post-log data, the weighted least squares formulation is employed. Regularization can be used jointly with the hybrid noise model for regularized image reconstruction. Existing iterative optimization algorithms, such as OS-SPS algorithm and its accelerated versions by the momentum approach, can be used to solve the optimization problem.

Figure 4:
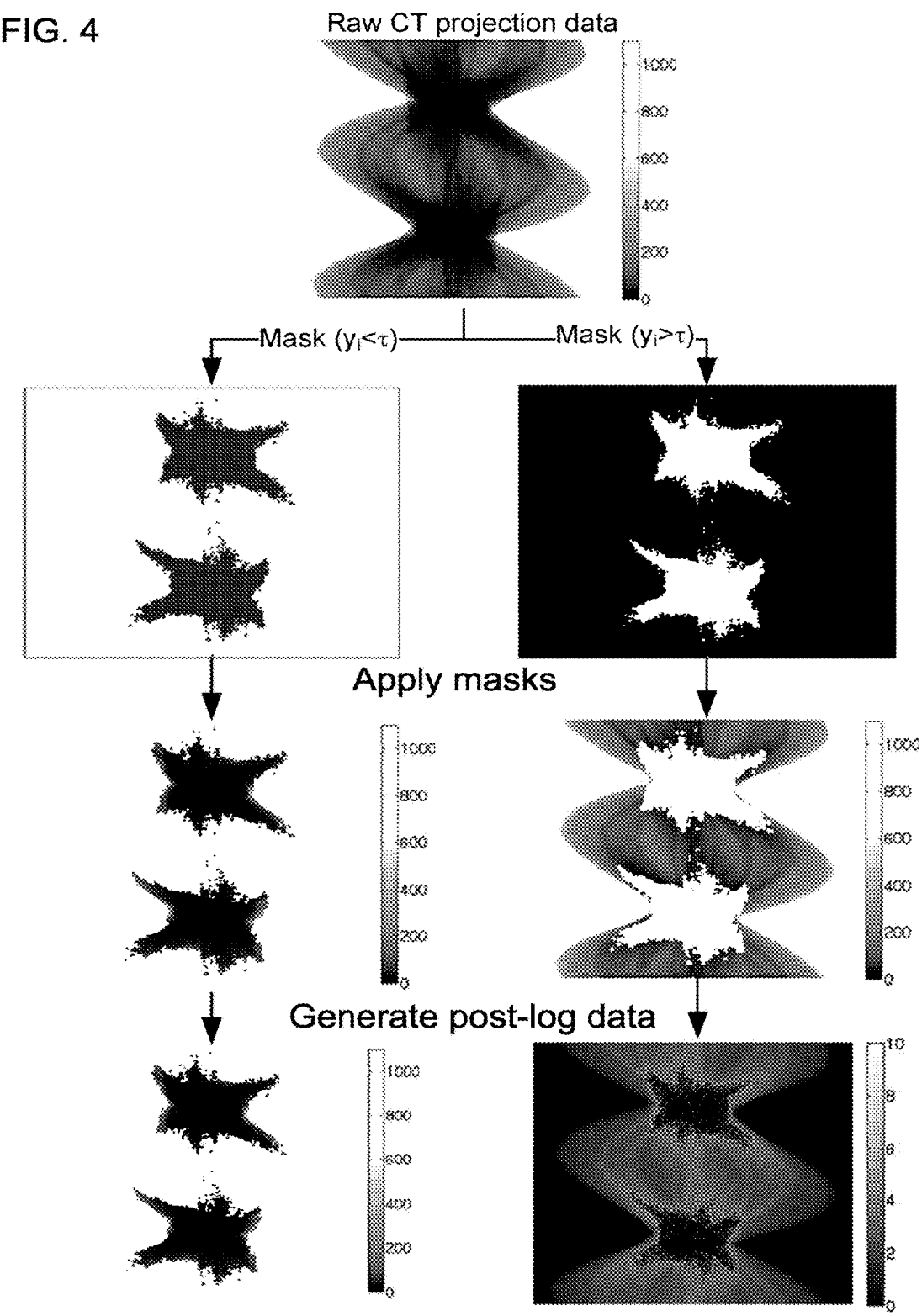
FIG. 4 shows a graphical representation of the method for hybrid pre-log and post-log IR that masks the pre-log data and then generates post-log data, according to one implementation.

FIG. 4 shows an implementation of method 100 to calculate the cost function in Eq. (12). The implementation shown in FIG. 4 differs from the implementation shown in FIGS. 2A and 2B because the masks are applied to the pre-log data before generating the partial post-log data from the pre-log data that has been masked by the post-log mask. In general, any order of operations can be used to calculate the cost function in Eq. (12). FIG. 4 does not show the steps corresponding to the optimization to generate the reconstructed image.

As would be understood by one of ordinary skill in the art, the implementations of method 100 described above can be modified in several ways.

First, various formulations can be implemented as the processing methods for the pre-log data and post-log data respectively. For example, Eq. (12) applies a PWLS formulation, but the PWLS formulation can be substituted with other methods (e.g., with a filtered back projection formulation in which the weights $w_i$ are made to be equal one with another). Further, when the noise between pixels is correlated, then the weighted inner product of the form $(\hat{I}-Ax)^T W(\hat{I}-Ax)$ can be used, wherein W is the weight matrix in which correlations are represented by off-diagonal terms. Additionally, as would be understood by one of ordinary skill in the art, the pre-log formulation can be modified according to various noise models, such as those discussed in the fore-going.

Second, the threshold criteria can be modified to account for beam-hardening instead of, or in addition to, the electronic noise level and/or the signal-to-noise ratio. Thus, other threshold criteria can be chosen for sorting the projection data into bins for pre-log or post-log data, and these other threshold criteria can be based on the impact of the beam-hardening on the projection data. If a pixel of the projection data is highly impacted by beam-hardening (e.g., passing through high-attenuation mediums, such as contrast agent and bone), it is assigned to the pre-log data, and those pixels not assigned to the pre-log data are assigned to the post-log data.

For example, in certain implementations, the beam-hardening effect on the projection data can be determined in the image domain by: (i) quickly reconstructing a first image (e.g., by downsampling and using a non-iterative filtered back-projection method), (ii) using a threshold and region-growing method to determine regions of high-attenuation mediums, such as contrast agent and bone, within the coarse reconstructed image to generate an image-domain mask, (iii) upsampling the image-domain mask, and (iv) forward-projecting the upsampled image-domain mask to generate projection/sinogram domain masks similar to those shown in FIGS. 3C and 3D. In certain implementations, the forward-projection process can include additional threshold criteria, such that projection pixels corresponding to line trajectories passing through a predefined number of high attenuation image pixels are determined to be pre-log pixels in the projection domain.

It is noted that, in certain implementations of the pre-log data processing, multiplicative physical corrections, such as beam hardening, detector normalization, and X-ray reference fluence fluctuation, are included in the model of the system matrix. However, for the post-log data processing, these multiplicative physical corrections are pre-corrected in the post-log data themselves. Additionally, additive physical corrections, such as scatter and electronic dark current, are incorporated in the pre-log data model but are pre-corrected in post-log data processing.

Figure 5:
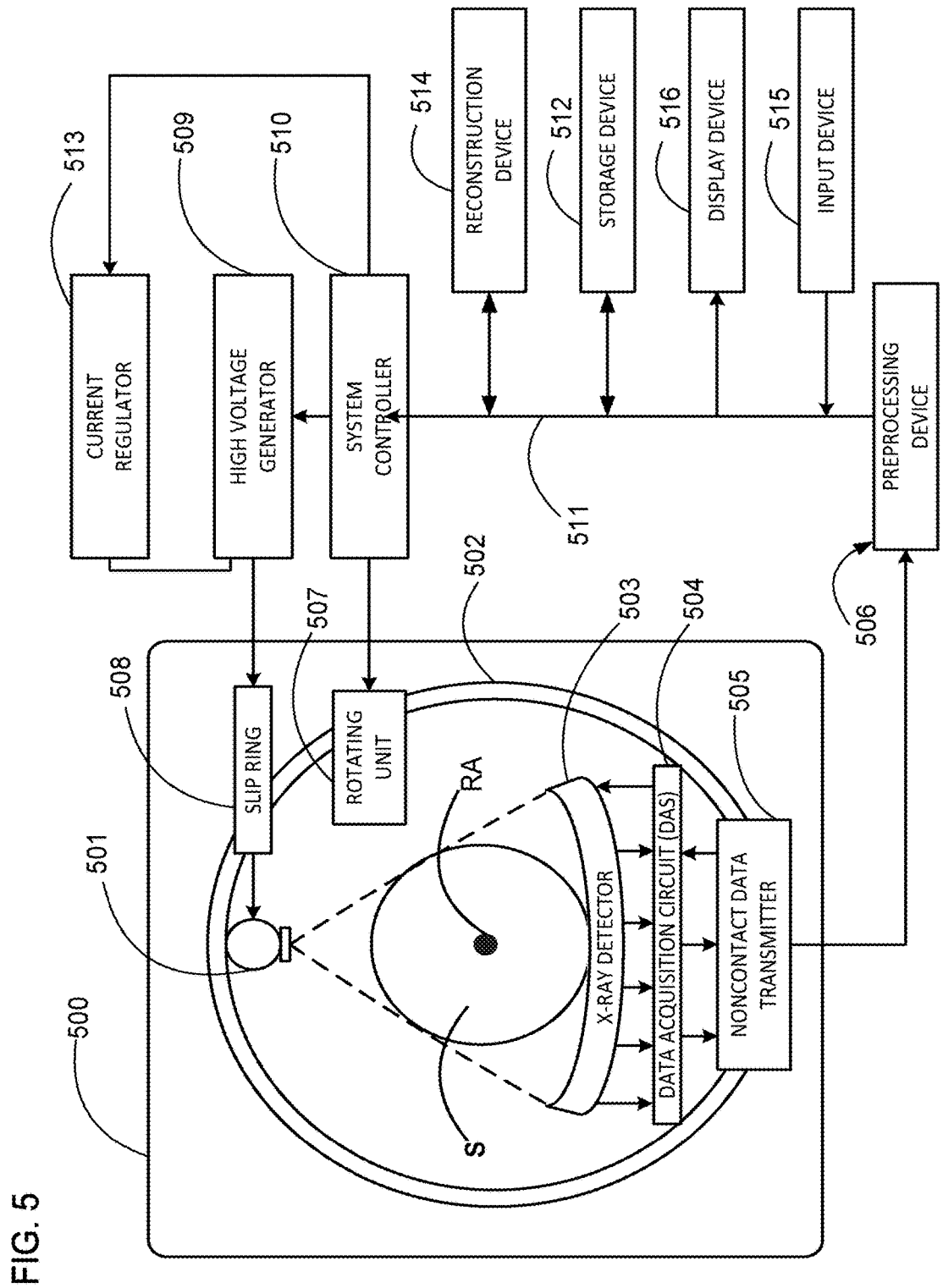
FIG. 5 shows a schematic of an implementation of a CT scanner, according to one implementation.

FIG. 5 illustrates an implementation of the radiography gantry included in a CT apparatus or scanner. As shown in FIG. 5, a radiography gantry 500 is illustrated from a side view and further includes an X-ray tube 501, an annular frame 502, and a multi-row or two-dimensional-array-type X-ray detector 503. The X-ray tube 501 and X-ray detector 503 are diametrically mounted across an object OBJ on the annular frame 502, which is rotatably supported around a rotation axis RA. A rotating unit 507 rotates the annular frame 502 at a high speed, such as 0.4 sec/rotation, while the object OBJ is being moved along the axis RA into or out of the illustrated page.

The first embodiment of an X-ray computed tomography (CT) apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, which is currently the mainstream, will be exemplified.

The multi-slice X-ray CT apparatus further includes a high voltage generator 509 that generates a tube voltage applied to the X-ray tube 501 through a slip ring 508 so that the X-ray tube 501 generates X-rays. The X-rays are emitted towards the object OBJ, whose cross sectional area is represented by a circle. For example, the X-ray tube 501 having an average X-ray energy during a first scan that is less than an average X-ray energy during a second scan. Thus, two or more scans can be obtained corresponding to different X-ray energies. The X-ray detector 503 is located at an opposite side from the X-ray tube 501 across the object OBJ for detecting the emitted X-rays that have transmitted through the object OBJ. The X-ray detector 503 further includes individual detector elements or units.

The CT apparatus further includes other devices for processing the detected signals from X-ray detector 503. A data acquisition circuit or a Data Acquisition System (DAS) 504 converts a signal output from the X-ray detector 503 for each channel into a voltage signal, amplifies the signal, and further converts the signal into a digital signal. The X-ray detector 503 and the DAS 504 are configured to handle a predetermined total number of projections per rotation (TPPR).

The above-described data is sent to a preprocessing device 506, which is housed in a console outside the radiography gantry 500 through a non-contact data transmitter 505. The preprocessing device 506 performs certain corrections, such as sensitivity correction on the raw data. A memory 512 stores the resultant data, which is also called projection data at a stage immediately before reconstruction processing. The memory 512 is connected to a system controller 510 through a data/control bus 511, together with a reconstruction device 514, input device 515, and display 516. The system controller 510 controls a current regulator 513 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 501 and the X-ray detector 503 are diametrically mounted on the annular frame 502 and are rotated around the object OBJ as the annular frame 502 is rotated about the rotation axis RA. In the fourth-generation geometry system, the detectors are fixedly placed around the patient and an X-ray tube rotates around the patient. In an alternative embodiment, the radiography gantry 500 has multiple detectors arranged on the annular frame 502, which is supported by a C-arm and a stand.

The memory 512 can store the measurement value representative of the irradiance of the X-rays at the X-ray detector unit 503. Further, the memory 512 can store a dedicated program for executing the hybrid method 100 for CT image reconstruction discussed herein.

The reconstruction device 514 can execute the hybrid method 100 for CT image reconstruction discussed herein. Further, reconstruction device 514 can execute pre-reconstruction processing image processing such as volume rendering processing and image difference processing as needed.

The pre-reconstruction processing of the projection data performed by the preprocessing device 506 can include correcting for detector calibrations, detector nonlinearities, and polar effects, for example.

Post-reconstruction processing performed by the reconstruction device 514 can include filtering and smoothing the image, volume rendering processing, and image difference processing as needed. The image reconstruction process can use any of the implementations for image reconstruction using method 100 discussed or contemplated herein. The reconstruction device 514 can use the memory to store, e.g., projection data, reconstructed images, calibration data and parameters, and computer programs.

The reconstruction device 514 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 512 can be non-volatile, such as ROM, EPROM, EEPROM or FLASH memory. The memory 512 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 514 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 516. The display 516 can be an LCD display, CRT display, plasma display, OLED, LED or any other display known in the art.

The memory 512 can be a hard disk drive, CD-ROM drive, DVD drive, FLASH drive, RAM, ROM or any other electronic storage known in the art.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
    processing circuitry configured to
        obtain projection data representing an intensity of X-ray radiation detected at a plurality of detector elements, the projection data including a plurality of projection images, and each projection image including pixels corresponding to respective detector elements of the plurality of detector elements,
        categorize pixels of a projection image of the obtained projection data into a first subset and a second subset, the first subset including one or more pixels of the projection image representing respective detection values that satisfy a predefined criterion, and the second subset including one or more pixels of the projection image representing detection values that do not satisfy the predefined criterion, and
        iteratively reconstruct a reconstructed image by adjusting pixel values of the reconstructed image to minimize a value of an optimization function, wherein the optimization function takes on a pre-log form of the optimization function for pixels in the first subset, and, for pixels in the second subset, takes on a post-log form of the optimization function, which is different from the pre-log form of the optimization function.

2. The apparatus according to claim 1, wherein the processing circuitry is further configured to
    generate a first mask and a second mask such that the first mask represents the first subset including the one or more pixels of the projection image that satisfy the predefined criterion, and the second subset represents the second subset including the one or more pixels of the projection image that do not satisfy the predefined criterion, and
    perform the categorizing of the pixels of a projection in to the first subset and the second subset image using the first mask and the second mask.

3. The apparatus according to claim 2, wherein the processing circuitry is further configured to generate the first mask and the second mask such that the predefined criterion is that the first mask represents values of another projection data that are less than a value of a threshold, and the second subset represents values of the another projection data that are greater than the value of the threshold.

4. The apparatus according to claim 3, wherein the processing is further configured to generate the first mask and the second mask using the another projection data, and the another projection data is one of a reprojection of a preliminary image reconstructed from the projection data, the projection data after the projection data is denoised, and the projection data after the projection data is filtered.

5. The apparatus according to claim 1, wherein the processing circuitry is further configured to iteratively reconstruct a reconstructed image using, on the second subset, the post-log form of the optimization function that includes
    calculating a logarithm of the values of the second subset of the projection data to generate post-log data, and
    calculating the optimization function based on a difference between the post-log data and the reconstructed image operated on using a system matrix.

6. The apparatus according to claim 5, wherein the processing circuitry is further configured to iteratively reconstruct a reconstructed image using the post-log form of the optimization function that includes using a penalized-weighted-least-squares formulation to sum values of the difference between the post-log data and the reconstructed image operated on using the system matrix.

7. The apparatus according to claim 1, wherein the processing circuitry is further configured to iteratively reconstruct a reconstructed image using, on the first subset, the pre-log form of the optimization function that uses a log likelihood function of a shifted-Poisson model to calculate a difference between the first subset of the projection data and the reconstructed image.

8. The apparatus according to claim 1, wherein the processing circuitry is further configured to categorize pixels of the projection image of the obtained projection data into the first subset and the second subset using the predefined criterion based on a threshold value that is calculated using a predefined function of a variance of an electronic noise of the plurality of detector elements.

9. The apparatus according to claim 1, wherein the processing circuitry is further configured to categorize pixels of the projection image of the obtained projection data into the first subset and the second subset using a threshold value that is calculated using a predefined function of a variance of an electronic noise of the plurality of detector elements and an X-ray count rate and/or background event rate at the plurality of detector elements.

10. The apparatus according to claim 1, wherein the processing circuitry is further configured to iteratively reconstruct the reconstructed image using the optimization function that includes a regularization term representing a penalty for roughness of the reconstructed image.

11. The apparatus according to claim 10, wherein the processing circuitry is further configured to iteratively reconstruct the reconstructed image using the regularization term that is one or more of a Huber regularization term, a quadratic regularization term, a patch-based regularization term, and a total variation minimization regularization term.

12. The apparatus according to claim 1, wherein the processing circuitry is further configured to iteratively reconstruct the reconstructed image by adjusting pixel values of the reconstructed image using one or more of a separable paraboloidal surrogate method, ordered subsets method, a gradient descent method, an augmented-Lagrangian method, alternating direction-method-of-multiplier method, a Nesterov method, a preconditioned- gradient-descent method.

13. The apparatus according to claim 1, wherein the pre-log form of the optimization function uses one or more of Gaussian noise model, a Poisson noise model, a compound Poisson noise model, a shifted-Poisson noise model, and a Gaussian-Poisson noise model.

14. An apparatus, comprising:
an X-ray source to radiate X-rays;
a plurality of detector elements, each configured to
  detect the X-rays that are radiated from the X-ray source, and
  generate projection data representing an intensity of the X-rays detected at the plurality of detector elements, the projection data including a plurality of projection images, and each projection image including pixels corresponding to respective detector elements of the plurality of detector elements; and
processing circuitry configured to
  obtain the projection data representing the intensity of the X-rays detected at the plurality of detector elements,
  categorize pixels of a projection image of the obtained projection data into a first subset and a second subset, the first subset including one or more pixels of the projection image representing respective detection values that satisfy a predefined criterion, and the second subset including one or more pixels of the projection image representing detection values that do not satisfy the predefined criterion, and
  iteratively reconstruct a reconstructed image by adjusting pixel values of the reconstructed image to minimize a value of an optimization function, wherein
    the optimization function takes on a pre-log form of the optimization function for pixels in the first subset, and, for pixels in the second subset, takes on a post-log form of the optimization function, which is different from the pre-log form of the optimization function.

15. The apparatus according to claim 14, wherein the post-log form of the optimization function includes
  calculating a logarithm of the pixel values of the projection to generate post-log data, and
  calculating a difference between the post-log data and the reconstructed image operated on using a system matrix.

16. The apparatus according to claim 15, wherein the post-log form of the optimization function further includes using a penalized-weighted-least-squares formulation to sum values of the difference between the post-log data and the reconstructed image operated on using the system matrix.

17. The apparatus according to claim 14, wherein the pre-log form of the optimization function uses a log likelihood function of a shifted-Poisson model to calculate a difference between the first subset of the projection data and the reconstructed image.

18. The apparatus according to claim 14, wherein the optimization function further includes a regularization term representing penalty for roughness of the reconstructed image.

19. A method, comprising:
obtaining projection data representing an intensity of X-ray radiation detected at a plurality of detector elements, the projection data including a plurality of projection images, and each projection image including pixels corresponding to respective detector elements of the plurality of detector elements,
categorizing pixels of a projection image of the obtained projection data into a first subset and a second subset, the first subset including one or more pixels of the projection image representing respective detection values that satisfy a predefined criterion, and the second subset including one or more pixels of the projection image representing detection values that do not satisfy the predefined criterion, and
iteratively reconstructing a reconstructed image by adjusting pixel values of the reconstructed image to minimize a value of an optimization function, wherein
the optimization function takes on a pre-log form of the optimization function for pixels in the first subset, and, for pixels in the second subset, takes on a post-log form of the optimization function, which is different from the pre-log form of the optimization function.

20. A non-transitory computer readable storage medium including executable instruction, wherein the instructions, when executed by circuitry, cause the circuitry to perform the method according to claim 19.

* * * * *